(12) United States Patent
Sasaki et al.

(10) Patent No.: US 9,156,014 B2
(45) Date of Patent: Oct. 13, 2015

(54) TWO-COMPONENT MIXING CONTAINER WITH COMMUNICATION PASSAGE OF LIQUID-TIGHT STRUCTURE

(71) Applicants: PENTEL CO., LTD., Tokyo (JP); SHOFU INC., Kyoto-shi, Kyoto (JP)

(72) Inventors: Tsukasa Sasaki, Soka (JP); Ryouji Takei, Soka (JP); Toshiyuki Nakatsuka, Kyoto (JP); Shuji Sakamoto, Kyoto (JP); Satoshi Takano, Kyoto (JP); Satoshi Kawahara, Kyoto (JP)

(73) Assignee: SHOFU INC., Kyoto-Shi (JP)

( * ) Notice: Subject to any disclaimer, the term of this patent is extended or adjusted under 35 U.S.C. 154(b) by 31 days.

(21) Appl. No.: 14/225,913

(22) Filed: Mar. 26, 2014

(65) Prior Publication Data

US 2015/0090615 A1   Apr. 2, 2015

(30) Foreign Application Priority Data

Sep. 30, 2013   (JP) ................................ 2013-205359

(51) Int. Cl.
| | |
|---|---|
| *B01F 15/02* | (2006.01) |
| *A61C 5/06* | (2006.01) |
| *B05C 17/005* | (2006.01) |
| *B65D 81/32* | (2006.01) |
| *B05B 11/00* | (2006.01) |

(52) U.S. Cl.
CPC ............. *B01F 15/0279* (2013.01); *A61C 5/064* (2013.01); *A61C 5/066* (2013.01); *A61C 5/068* (2013.01); *B65D 81/3255* (2013.01); *B05B 11/0029* (2013.01); *B05B 11/0078* (2013.01); *B05C 17/00503* (2013.01); *B05C 17/00596* (2013.01); *B65D 81/3222* (2013.01)

(58) Field of Classification Search
CPC ............ B01F 15/0279; B65D 81/3222; B65D 81/3225; A61C 5/064; A61C 5/068
USPC ..................... 206/219, 221, 63.5; 215/DIG. 8; 222/145.5, 129; 433/90
See application file for complete search history.

(56) References Cited

U.S. PATENT DOCUMENTS

| | | | |
|---|---|---|---|
| 5,172,807 A | 12/1992 | Dragan et al. | |
| 8,403,180 B2 * | 3/2013 | Nakatsuka et al. | 222/145.5 |
| 2011/0005945 A1 | 1/2011 | Nakatsuka et al. | |
| 2011/0017777 A1 | 1/2011 | Nakatsuka et al. | |

FOREIGN PATENT DOCUMENTS

| | | |
|---|---|---|
| DE | 4232062 | 4/1993 |
| EP | 1759657 | 3/2007 |

(Continued)

OTHER PUBLICATIONS

European Search Report dated Feb. 12, 2015, 5 pages.

*Primary Examiner* — Anthony Stashick
*Assistant Examiner* — Mollie Llewellyn
(74) *Attorney, Agent, or Firm* — Rankin, Hill & Clark LLP

(57) ABSTRACT

Provided is a two-component mixing container in which a communication passage may be formed between a partition wall member and a second-component containing member without the need for a high processing precision and a high assembly precision. A columnar portion provided at the central portion of a second bottom wall portion of a partition wall member and a circular through hole provided in the central portion of a third bottom wall portion of a second-component containing member are fitted. A first communication passage and a second communication passage are communicated with each other, using a fitting surface formed between the columnar portion and the circular through hole.

2 Claims, 23 Drawing Sheets

(56) References Cited

FOREIGN PATENT DOCUMENTS

| | | |
|---|---|---|
| JP | H05-192381 | 8/1993 |
| JP | 2007-061633 | 3/2007 |
| JP | 4956616 | 6/2012 |
| JP | 5112438 | 1/2013 |

* cited by examiner

TWO-COMPONENT MIXING CONTAINER WITH COMMUNICATION PASSAGE OF LIQUID-TIGHT STRUCTURE

FIELD OF THE INVENTION

The present invention relates to a two-component mixing container configured to contain two kinds of components in isolation from each other, and to allow the two kinds of components to be mixed together in the two-component mixing container before being discharged, when in use.

BACKGROUND OF THE INVENTION

Japanese Patent No. 4956616 (Patent Document 1) and Japanese Patent No. 5112438 (Patent Document 2), which are the patents owned by the applicant of the present invention, each disclose a conventional example of a two-component mixing container such as a dental cement capsule. In this two-component mixing container, a powder material and a liquid material are contained in isolation from each other as two kinds of chemicals, and the powder material and the liquid material are discharged after having been mixed together in the two-component mixing container. FIGS. 19 and 20A to 20C are respectively FIGS. 10 and 11A to 11C in Patent Document 1. The structure of the conventional two-component mixing container will be described below, using these drawings. The conventional two-component mixing container includes a housing 8, a nozzle 16, a partition wall member (12, 18), a second-component containing member 13, and a piston member 19. The housing 8 includes a first cylindrical portion 10 having a first opening portion at one end thereof and a first bottom wall portion 11 closing the other end of the first cylindrical portion 10. Then, the housing 8 includes in its inside a mixing chamber 5 configured to contain a first component and to mix the first component and a second component when the second component is injected from the one end of the first cylindrical portion 10. The housing 8 also has a discharge port 23 in the first bottom wall portion 11. The discharge port 23 is configured to discharge a mixture of the first component and the second component from the mixing chamber 5. The nozzle 16 is provided at the first bottom wall portion 11 of the housing 8. A mounting structure of the nozzle 16 is configured to dispose the nozzle 16 at a first position which causes the nozzle to close the discharge port 23 before the mixture is discharged from the discharge port 23 and to dispose the nozzle 16 at a second position which allows the discharge port and a passage of the nozzle to communicate with each other when the mixture is discharged from the discharge port 23.

A partition wall member (12, 18) is slidably held in the housing 8. The partition wall member (12, 18) includes a second cylindrical portion 18 having a second opening portion at one end thereof, a second bottom wall portion closing the other end of the second cylindrical portion 18, and a partition wall portion 12 provided at the second bottom wall portion, whereby the partition wall portion slides liquid-tightly inside the mixing chamber 5. Then, the second-component containing member 13 is fitted in the partition wall member (12, 18) such that the second-component containing member 13 may rotate about an axial line X. The second-component containing member 13 includes a third cylindrical portion having a third opening portion at one end thereof and a third bottom wall portion closing the other end of the third cylindrical portion, and includes in its inside a second-component containing chamber 3 configured to contain the second component. The second bottom wall portion (12) of the partition wall member (12, 18) is formed with a first communication passage 20, and the third bottom wall portion of the second-component containing member 13 is formed with a second communication passage 21. When the second-component containing member 13 rotates about the axial line X by a predetermined angle and then the second-component containing member 13 and the partition wall member (12, 18) come into a predetermined positional relationship, the first communication passage 20 and the second communication passage 21 communicate with each other, thereby allowing the second component to flow into the mixing chamber 5. The piston member 19 includes a piston portion located at one end of the piston member 19 and an operating rod portion located at the other end of the piston member 19. The piston portion is configured to be inserted into the third cylindrical portion from the third opening portion of the second-component containing member 13 and liquid-tightly slide inside the third cylindrical portion. The operating rod portion projects out from the third opening portion.

Before an operation of mixing the first component and the second component is started, the conventional two-component mixing container maintains a holding state in which the partition wall member (12, 18) is held in a retracted position so as to form the mixing chamber 5 in the housing 8. By performing a predetermined first operation (operation of rotation about the axial line X) on the operating rod portion of the piston member 19 in this state, the first communication passage 20 and the second communication passage 21 are aligned to communicate with each other. A communication passage (comprising the communication passages 20 and 21) is thereby formed between the second-component containing chamber 3 and the mixing chamber 5. Then, after the communication passage has been formed, the piston member 19 is moved toward the first bottom wall portion 11 to inject the second component within the second-component containing chamber 3 into the mixing chamber 5 through the communication passage (comprising the communication passages 20 and 21) that has been formed. Then, by performing an operation (second operation) of rotation about the axial line X on the piston member 19, the holding state of the partition wall member (12, 18) is released. The nozzle 16 is then disposed at the second position (position where the passage of the nozzle 16 and the discharge port 23 communicate with each other) from the first position (position shown in FIG. 19). The piston member 19 is further moved toward the first bottom wall portion 11 in this state to discharge the mixture to an outside through the nozzle 16. An engagement relationship between the housing 8 and the partition wall member (12, 18) is achieved by engagement between a projection (24) and a guide groove (25). An engagement relationship between the partition wall member (12, 18) and the second-component containing member 13 is achieved by engagement between a projection (26) and a guide groove (27). An engagement relationship between the second-component containing member 13 and the piston member 19 is achieved by a projection (28) and a guide groove (29). These projections (24, 26, 28) and guide grooves (25, 27, 29) are shown in FIG. 20 (corresponding to FIG. 11 in Patent Document 1).

SUMMARY OF THE INVENTION in the conventional two-component mixing container, the partition wall portion 12 formed by deformation of the second bottom wall portion of the partition wall member (12, 18) curves to be convex toward the third bottom wall portion of the second-component containing member 13. Then, the third bottom wall portion of the second-component containing member 13 curves to be convex toward the partition wall portion 12 (second bottom wall portion 12) of the partition wall member (12, 18). Consequently, in order to align the first communication passage 20 and the second communication passage 21 to ensure the communication state between the first communication passage 20 and the second communication passage 21, it is necessary to enhance processing precision of each of the partition wall member (12, 18) and the second-component containing member 13 and also to increase assembly precision of each component.

An object of the present invention is to provide a two-component mixing container in which a communication passage may be formed between a partition wall member and a second-component containing member without the need for a high processing precision and a high assembly precision.

A two-component mixing container, improvement of which is aimed at by the present invention comprises: a housing, a nozzle, a partition wall member, a second-component containing member, a piston member, and a holding structure. The housing includes a first cylindrical portion having a first opening portion at one end thereof and a first bottom wall portion closing the other end of the first cylindrical portion. The housing also includes in its inside a mixing chamber configured to contain a first component and to mix the first component and a second component when the second component is injected from the one end of the first cylindrical portion. The housing also includes in the first bottom wall portion a discharge port configured to discharge a mixture of the first component and the second component from the mixing chamber. Herein, the "first component" and the "second component" each mean a material in a liquid state, a paste state, a powder state, or the like having a property capable of being discharged, and are each formed of at least one kind of material (including both of a case of only one kind of material and a case of a plurality of kinds of materials). The nozzle is provided at the housing and is configured to discharge the mixture, whereby the mixture comes out of the discharge port and is discharged through the nozzle. The partition wall member is held in the first cylindrical portion and includes a second cylindrical portion having a second opening portion at one end thereof, a second bottom wall portion closing the other end of the second cylindrical portion and a partition wall portion provided at the second bottom wall portion and configured to liquid-tightly slide in the mixing chamber. The second-component containing member is held in the second cylindrical portion and includes a third cylindrical portion having a third opening portion at one end thereof and a third bottom wall portion closing the other end of the third cylindrical portion. The second-component containing member also includes in its inside a second-component containing chamber configured to contain the second component. The piston member includes a piston portion located at one end of the piston member and configured to be inserted into the third cylindrical portion from the third opening portion and to liquid-tightly slide in the third cylindrical portion, and an operating rod portion located at the other end of the piston member and projecting out from the third opening portion. The holding structure is configured to hold the partition wall member in a fixed state with respect to the housing until the second component is injected into the mixing chamber and to release the fixed state when the mixture is discharged through the nozzle. The second bottom wall portion of the partition wall member is formed with a first communication passage and the third bottom wall portion of the second-component containing member is formed with a second communication passage. The first communication passage and the second communication passage communicate with each other when the two-component containing member and the partition wall member come into a predetermined positional relationship, thereby allowing the second component to flow into the mixing chamber. In the two-component mixing container of the present invention, a columnar portion extending along the second cylindrical portion is unitarily formed with a central portion of the second bottom wall portion of the partition wall member. A circular through hole is formed in a central portion of the third bottom wall portion of the second-component containing member, whereby the columnar portion is fitted into the circular through hole. Then, the first communication passage is formed in the second bottom wall portion of the partition wall member and the columnar portion such that one end of the first communication passage opens in an outer surface of the columnar portion and the other end of the first communication passage opens in an outer wall surface of the second bottom wall portion. The second communication passage is formed in an inner wall of the third bottom wall portion of the second-component containing member such that one end of the second communication passage communicates with the circular through hole and the other end of the second communication passage opens toward the second-component containing chamber. The columnar portion and the circular through hole are shaped and sized such that the third cylindrical portion of the second-component containing member rotates with respect to the columnar portion in a liquid-tight state until the one end of the first communication passage and the one end of the second communication passage communicate with each other.

According to the present invention, the first communication passage and the second communication passage may be communicated with each other, using a fitting surface formed between the columnar portion provided at the central portion of the second bottom wall portion of the partition wall member and the circular through hole provided in the central portion of the third bottom wall portion of the second-component containing member. Consequently, the first communication passage and the second communication passage may be more reliably communicated with each other than in the conventional two-component mixing container. Further, a high processing precision is not needed for each of the partition wall member and the second-component containing member.

Preferably, a through hole for air extraction is formed in the second bottom wall portion of the partition wall member. The through hole is configured to communicate the mixing chamber and a gap between the second bottom wall portion and the third bottom wall portion of the second-component containing member. With this arrangement, the air extraction is performed using the gap. Thus, when injecting the second component into the mixing chamber, air extraction may be readily performed without preparing for a special structure.

BRIEF DESCRIPTION OF THE DRAWINGS

These and other objects and many of the attendant advantages of the present invention will be readily appreciated as the same becomes better understood by reference to the following detailed description when considered in connection with the accompanying drawings.

DETAILED DESCRIPTION OF PREFERRED EMBODIMENT

Figure 1A:
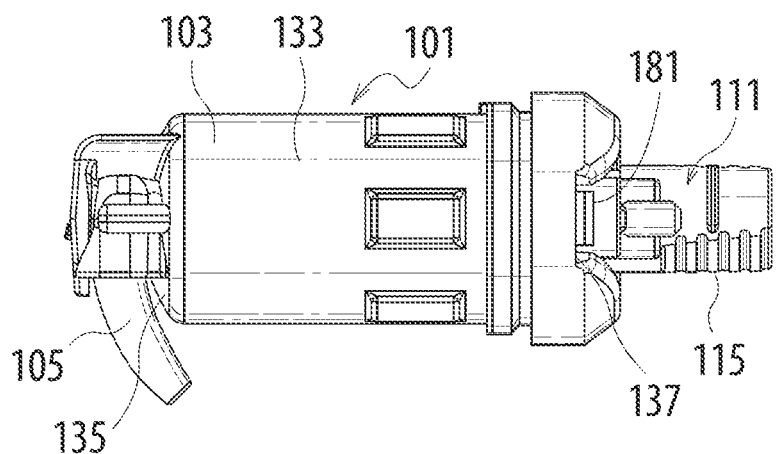
FIGS. 1A to 1D are respectively a front view, a right side view, a bottom view, and a left side view of an embodiment of a two-component mixing container of the present invention applied to a chemical mixing container.
Figure 1B:
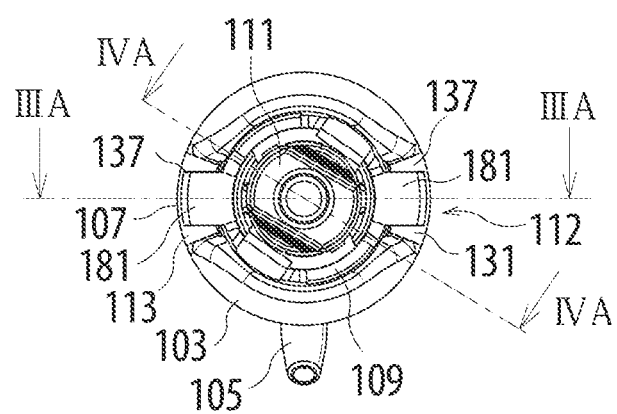
Figure 1C:
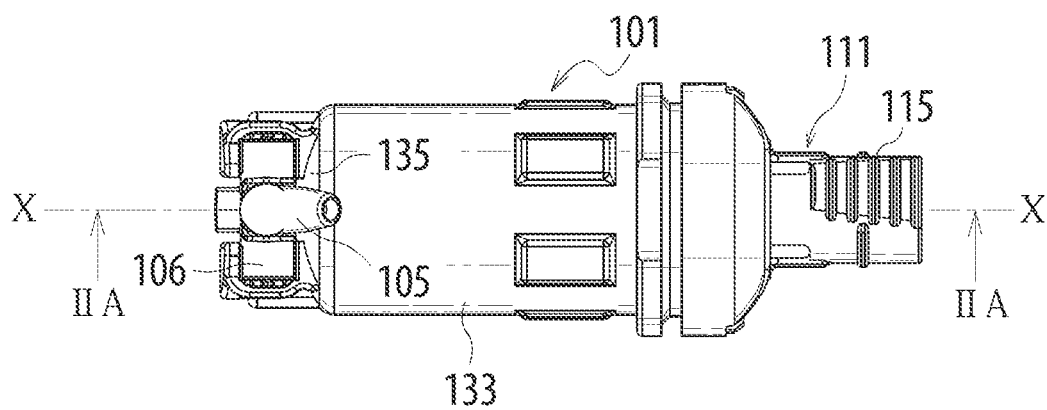
Figure 1D:
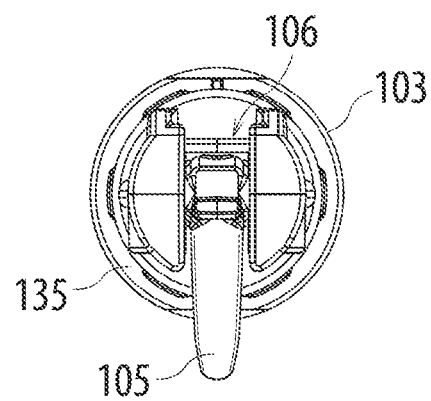
Figure 2A:
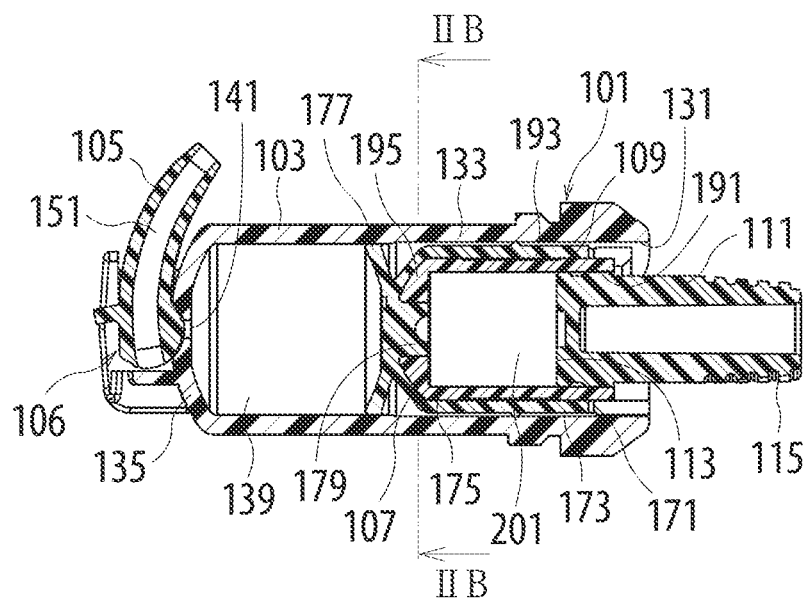
FIGS. 2A and 2B are respectively a sectional view taken along a line IIA-IIA in FIG. 1C and a sectional view taken along a line IIB-IIB in FIG. 2A.
Figure 2B:
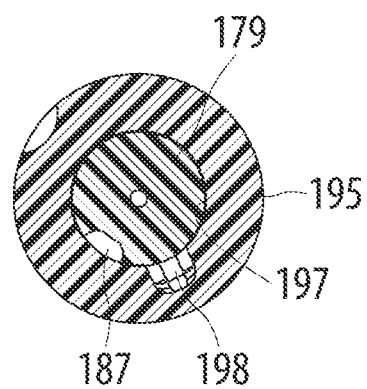
Figure 3A:
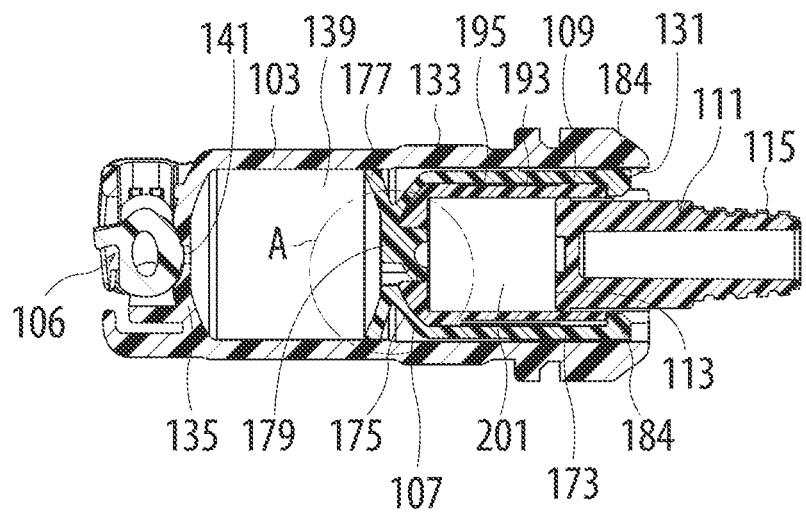
FIGS. 3A and 3B are respectively a sectional view taken along a line IIIA-IIIA in FIG. 1B and an enlarged view of a portion A in FIG. 3A.
Figure 3B:
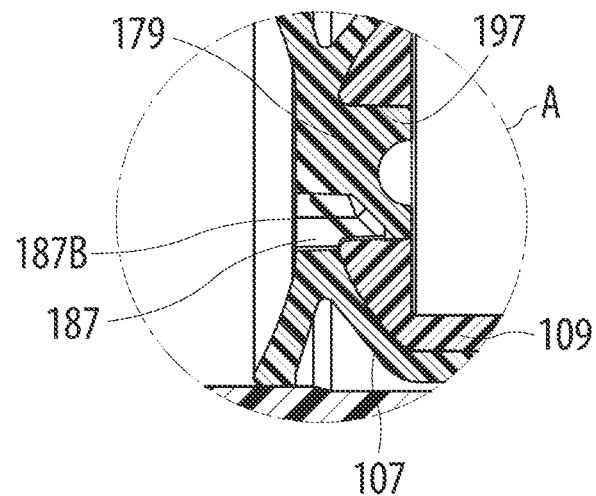
Figure 4A:
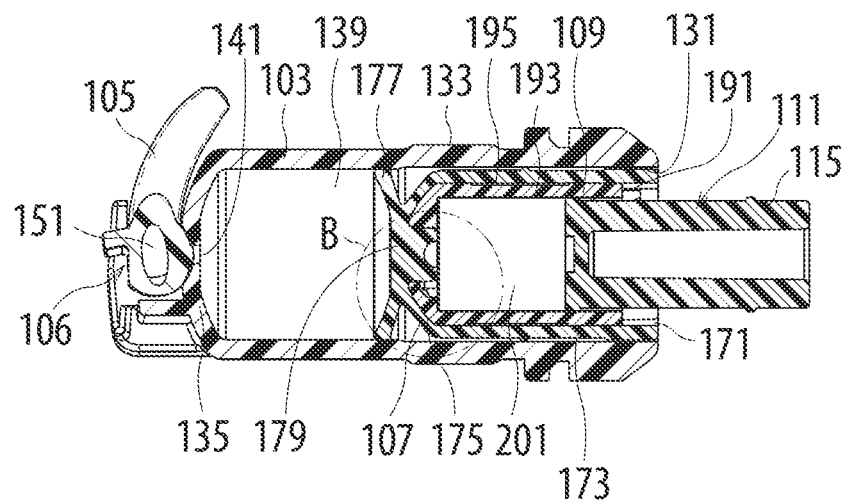
FIGS. 4A and 4B are respectively a sectional view taken along a line IVA-IVA in FIG. 1B and an enlarged view of a portion B in FIG. 4A.
Figure 4B:
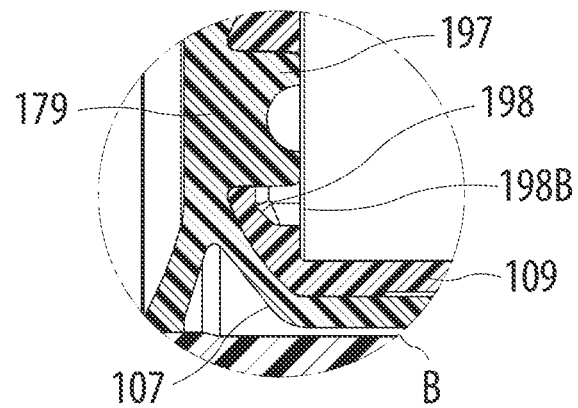

An example of an embodiment of a two-component mixing container of the present invention will be described below in detail with reference to drawings. FIGS. 1A to 1D are respectively a front view, a right side view, a bottom view, and a left side view of the embodiment of a two-component mixing container 101 of the present invention applied to a chemical mixing container. FIGS. 2A and 2B are respectively a sectional view taken along a line IIA-IIA in FIG. 1C and a sectional view taken along a line IIB-IIB in FIG. 2A. FIG. 3A is a sectional view taken along a line IIIA-IIIA in FIG. 1B. FIG. 3B is an enlarged view of a portion A in FIG. 3A. FIG. 4A is a sectional view taken along a line IVA-IVA in FIG. 1B, and FIG. 4B is an enlarged view of a portion A in FIG. 4A. The two-component mixing container 101 in this embodiment is configured to store two kinds of chemicals (components) for producing a dental material such as amalgam or a medical material such as bone cement, or, in particular, a powder material and a liquid material in isolation from each other, and to mix the two kinds of chemicals to discharge (eject) a desired mixture (or a reaction product), if necessary, when in use. The two-component mixing container 101 includes a housing 103 made of a resin (specifically made of polypropylene), a nozzle 105 formed of a resin, a nozzle mounting structure 106, a partition wall member 107 made of a resin, a second-component containing member 109 made of a resin, a piston member 111 made of a resin, and a holding structure 112. The two-component mixing container 101 shown in FIGS. 1A to 4B shows an unused state where the piston member 111 is not operated with two components (powder and liquid) not shown filled in the two-component mixing container 101.

The housing 103 includes a first cylindrical portion 133 having a first opening portion 131 at one end thereof and a first bottom wall portion 135 closing the other end of the first cylindrical portion 133. The housing 103 includes two recesses or concave portions 137 separated from each other at an interval of 180 degrees around the first opening portion 131. The housing 103 also includes in its inside a mixing chamber 139 configured to contain a first component (powder) and to mix the first component and a second component (liquid) when the second component is injected from a side of the one end of the first cylindrical portion 133. The housing 103 also has in the first bottom wall portion 135 a discharge port 141 configured to discharge a mixture of the first and second components from the mixing chamber 139. The nozzle 105 is provided at the housing 103 and configured to discharge the mixture, whereby the mixture comes out of the discharge port 141 and is discharged through the nozzle 105. The nozzle mounting structure 106 is configured to dispose the nozzle 105 at a first position which causes the nozzle to close the discharge port 141 before the mixture is discharged from the discharge port 141 and to dispose the nozzle 105 at a second position which allows the discharge port 141 and a passage 151 of the nozzle 105 to communicate with each other when the mixture is discharged from the discharge port 141. Details of the nozzle mounting structure 106 will be described later.

As shown in FIGS. 2A, 3A, 4A, and 5A to 5C, the partition wall member 107 is held in the first cylindrical portion 133 of the housing 103, and unitarily includes a second cylindrical portion 173 having a second opening portion 171 at one end thereof, a second bottom wall portion 175 closing the other end of the second cylindrical portion 173, and a partition wall portion 177 provided at the second bottom wall portion 175, whereby the partition wall portion slides liquid-tightly inside the mixing chamber 139. A columnar portion 179 extending along the second cylindrical portion 173 is unitarily formed with the central portion of the second bottom wall portion 175 of the partition wall member 107. A pair of projecting pieces 181 extending in a radial direction of the second cylindrical portion 173 are provided at end portions of the second cylindrical portion 173 of the partition wall member 107 on the side of the second opening portion 171. The pair of projecting pieces 181 are separated from each other by 180 degrees in a peripheral direction of the second cylindrical portion 173. The pair of projecting pieces 181 are fitted in a pair of concave portions 137 provided in the first cylindrical portion 133 when the partition wall member 107 is fitted in the housing 103. In this embodiment, the pair of projecting pieces 181 and the pair of concave portions 137 form the holding structure 112. The holding structure 112 is configured to hold the partition wall member 107 in a fixed state with respect to the housing 103 until the second component is injected into the mixing chamber 139 and to release the fixed state when the mixture is discharged through the nozzle 105. The pair of projecting pieces 181 are provided such that the pair of projecting pieces 181 are bent or get broken by pressing the piston member 111 toward the third bottom wall portion 195 of the second-component containing member 109 by a force of a predetermined level or higher. The piston member 111 will be described later. With this arrangement, the fixed state of the partition wall member 107 may be achieved using a simple structure. In addition, the fixed state of the partition wall member 107 is released by bending or breaking the pair of projecting pieces 181. Thus, an advantage of simplifying a structure for releasing the fixed state may be obtained. It may also be so arranged that three or more of the projecting pieces 181 and three or more of the concave portions 137 are provided.

Figure 6A:
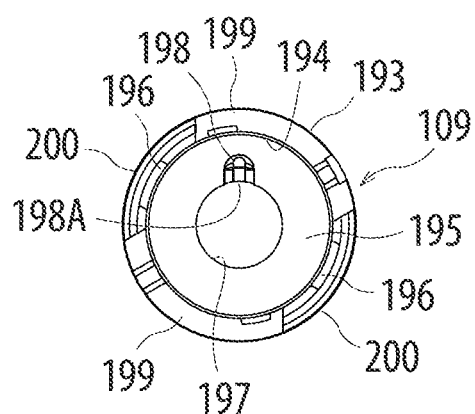
FIGS. 6A and 6B are respectively a plan view and a perspective view of a second-component containing member.
Figure 6B:
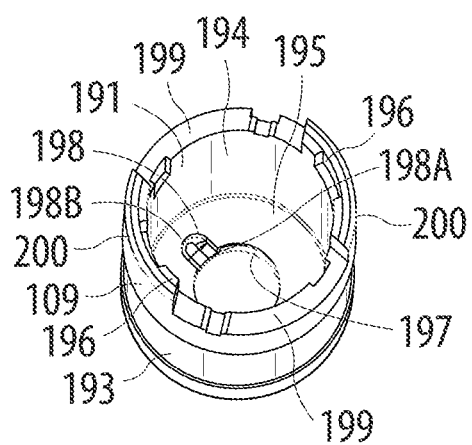

As shown in FIGS. 2A, 3A, and 4A, the second-component containing member 109 is fitted in the second cylindrical portion 173 of the partition wall member 107. The second-component containing member 109 is held in the second cylindrical portion 173, and includes a third cylindrical portion 193 having a third opening portion 191 at one end thereof and a third bottom wall portion 195 closing the other end of the third cylindrical portion 193, as shown in FIGS. 6A and 6B. Then, the second-component containing member 109 includes in its inside a second-component containing chamber 201 configured to contain the second component (liquid). Then, a circular through hole 197 is formed in the central portion of the third bottom wall portion 195 of the second-component containing member 109, whereby the columnar portion 179 is fitted into the circular through hole 197.

The following arrangements are made, as shown in FIGS. 3A, 5A to 5C, 6A and 6B, and 7C. The second cylindrical portion 173 of the partition wall member 107 is unitarily formed with a pair of engaging pieces 183 each including an engaging portion 184 which projects above the second opening portion 171. The third cylindrical portion 193 of the second-component containing member 109 is formed with a pair of recesses or concave portions 199 in an end portion of the third cylindrical portion on the side of the third opening portion 191, whereby the engaging portions 184 of the pair of engaging pieces 183 are engaged in the pair of concave portions 199. Then, the third cylindrical portion 193 of the second-component containing member 109 is provided with a pair of extended portions 200 between the pair of concave portions 199. A pair of fitting grooves 196 (FIG. 6A) are formed in the pair of extended portions. When the piston member 111 is rotated about an axial line X, the pair of extended portions 200 come into contact with the engaging portions 184 of the pair of engaging pieces 183 to define a rotation range of the second-component containing member 109.

As shown in FIGS. 2B, 3B, and 5A to 5C, a first communication passage 187 is formed in the second bottom wall portion 175 of the partition wall member 107 and the columnar portion 179 such that one end 187A of the first communication passage 187 opens in an outer surface of the columnar portion 179 and the other end 187B of the first communication passage 187 opens in an outer wall surface of the second bottom wall portion 175. Further, as shown in FIGS. 2B, 4B, and 6A and 6B, a second communication passage 198 is formed in an inner wall of the third bottom wall portion 195 of the second-component containing member 109 such that one end 198A of the second communication passage 198 communicates with the circular through hole 197 and the other end 198B of the second communication passage 198 opens toward the second-component containing chamber 201. That is, the second bottom wall portion 175 of the partition wall member 107 is formed with the first communication passage 187 and the third bottom wall portion 195 of the second-component containing member 109 is formed with the second communication passage 198. When the second-component containing member 109 and the partition wall member 107 come into a predetermined positional relationship, the first communication passage 187 and the second communication passage 198 communicate with each other, thereby allowing the second component to flow into the mixing chamber 139. The columnar portion 179 and the circular through hole 197 are shaped and sized such that the third cylindrical portion 193 of the second-component containing member 109 rotates with respect to the columnar portion 179 in a liquid-tight state until the one end 187A of the first communication passage 187 and the one end 198A of the second communication passage 198 communicate with each other. As shown in FIGS. 2A, 3A, and 4A, the piston member 111 includes a piston portion 113 located at one end thereof and an operating rod portion 115 located at the other end thereof. The piston portion 113 is configured to be inserted into the third cylindrical portion 193 from the third opening portion 191 of the second-component containing member 109 to liquid-tightly slide inside the third cylindrical portion 193. The operating rod portion 115 projects out from the third opening portion 191. A contact surface of the piston portion 113 configured to come into contact with an inner wall surface of the third cylindrical portion 193 of the second-component containing member 109 is set to be smaller in dimension than a contact portion 117 of each spring structure portion 119 as measured in a longitudinal direction of the operating rod portion. Consequently, contact resistance between the piston portion 113 and the inner wall surface of the third cylindrical portion 193 may be reduced. A force necessary for causing the piston member 111 to perform a linear motion operation may be therefore reduced.

Figure 7A:
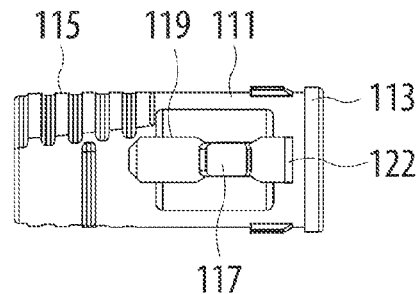
FIGS. 7A and 7B are respectively a plan view and a front view of a piston member.
Figure 7B:
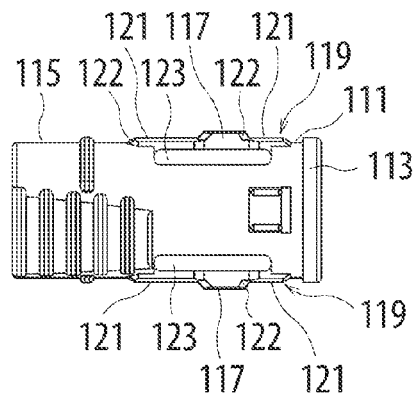
Figure 7C:
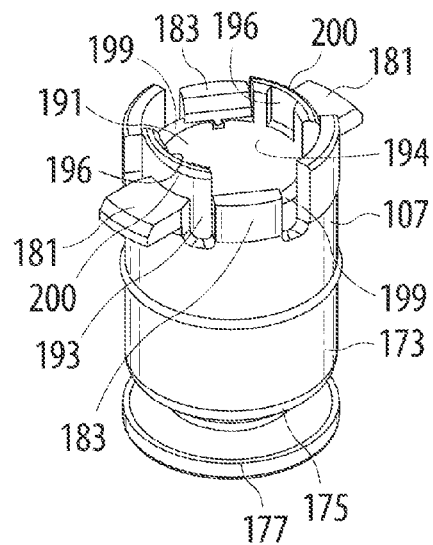
FIG. 7C is a perspective view showing a state where the partition wall member and the second-component containing member are combined before the piston member is inserted into the second-component containing member.
Figure 8A:
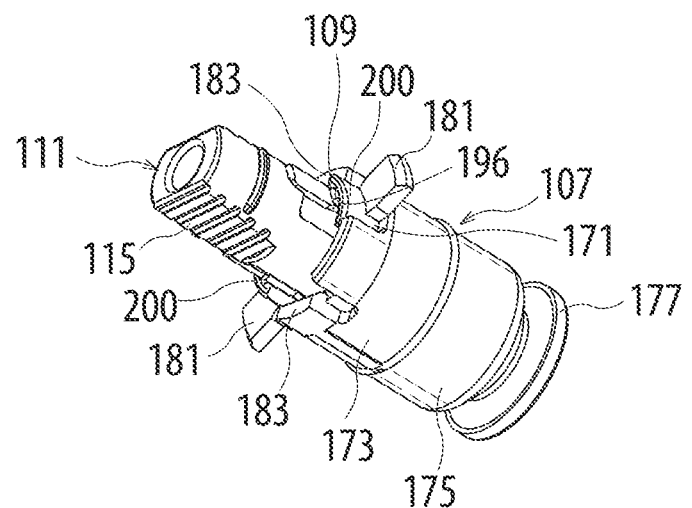
FIG. 8A is a perspective view of an assembly obtained by combining the piston member, the partition wall member, and the second-component containing member before the piston member is rotated.
Figure 8B:
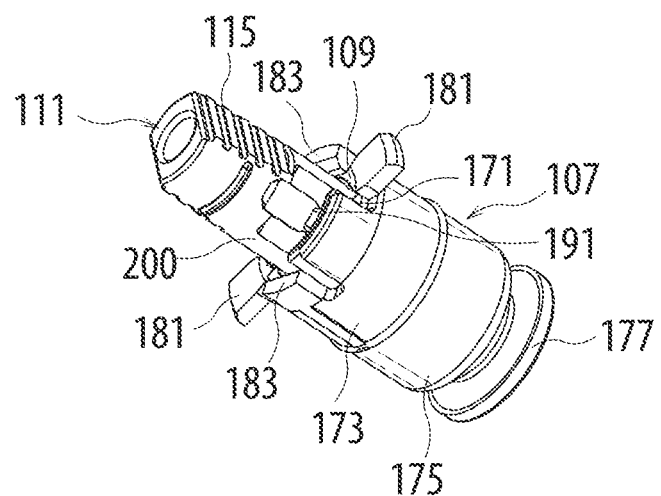
FIG. 8B is a perspective view of the assembly obtained by combining the piston member, the partition wall member, and the second-component containing member after the piston member has been rotated.
Figure 9A:
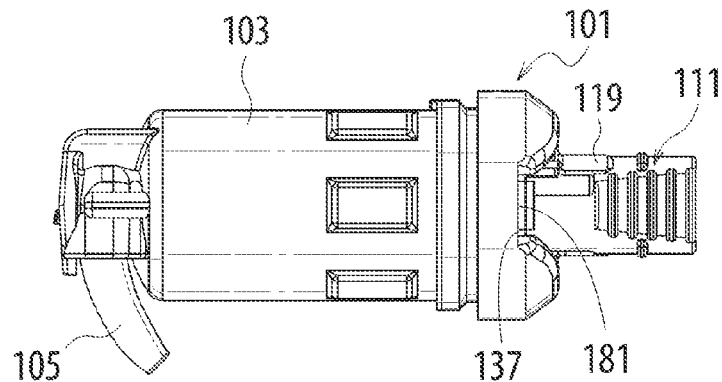
FIGS. 9A to 9C are respectively a front view, a right side view, and a bottom view of the two-component mixing container after the piston member has been rotated.
Figure 9B:
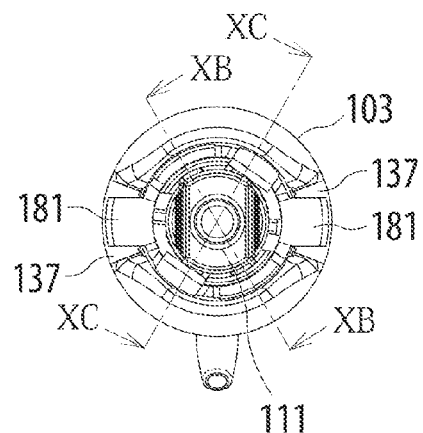
Figure 9C:
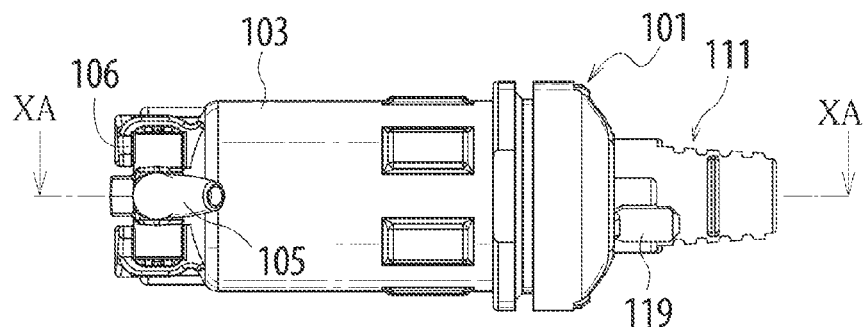
Figure 10A:
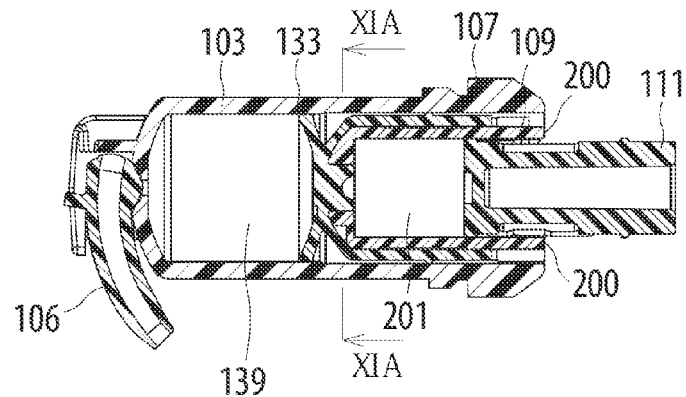
FIG. 10A is a sectional view taken along a line XA-XA in FIG. 9C.
Figure 10B:
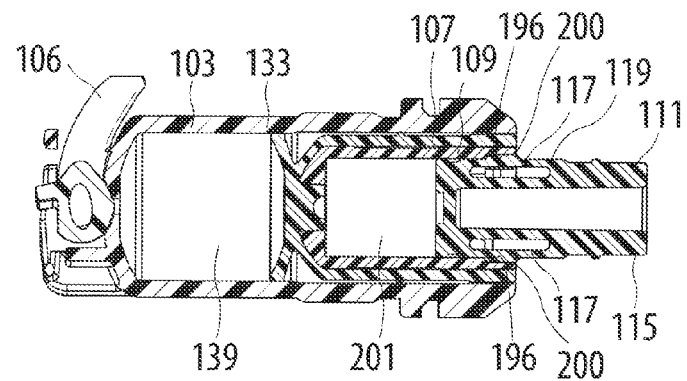
FIG. 10B is a sectional view taken along a line XB-XB in FIG. 9B.

As shown in FIGS. 7A, 7B, and 10B, a pair of the spring structure portions 119 are provided at the operating rod portion 115 of the piston member 111 and arranged at equal intervals in a peripheral direction of the piston portion 113. Each spring structure portion 119 includes the contact portion 117. The spring structure portion 119 is configured to deform by contact between an inner wall portion 194 of the third cylindrical portion 193 and the contact portion 117 and thereby impart a pressing force on the inner wall surface of the third cylindrical portion 193 when each spring structure portion 119 is inserted from the third opening portion 191 of the second-component containing member 109. The pair of fitting grooves 196 (FIGS. 7C and 10B) are formed in the third cylindrical portion 193 of the second-component containing member 109 at equal intervals in a peripheral direction of the third cylindrical portion 193. The contact portions 117 are fitted in the pair of fitting grooves 196 when the contact portions 117 are inserted into the pair of fitting grooves 196.

The piston member 111 used in this embodiment is unitarily formed of a synthetic resin material such as polypropylene. Then, each spring structure portion 119 includes a pair of arm portions 121 unitarily provided on both sides of the contact portion 117. A space 123 is formed between the arm portions 121 and the operating rod portion 115 to allow the arm portions 121 to deform. For that reason, a spring property may be imparted to each contact portion 117, using a simple structure. The contact portion 117 is supported by the pair of arm portions 121, in particular. Thus, reduction of mechanical strength of the spring structure portion 119 may be prevented. Further, a mold necessary for manufacturing the piston member 111 is simplified. Though two spring structure portions 119 are provided in this embodiment, three or more of the spring structure portions 119 may be of course provided. In that case, three or more of the fitting grooves 196 should be provided in the third cylindrical portion 193 of the second-component containing member 109.

Deformation of the pair of spring structure portions 119 at the piston member 111 causes the contact portions 117 at the spring structure portions 119 and the fitting grooves 196 in the third cylindrical portion 193 of the second-component containing member 109 to be brought into the fitting state. Even if the operating rod portion 115 of the piston member 111 is rotated in this state, the contact portions 117 do not get out of the fitting grooves 196.

The state shown in each of FIGS. 1 to 3 and FIG. 8A is a state where the contact portions 117 are fitted in the fitting grooves 196. When the operating rod portion 115 is rotated about the axial line X (refer to FIG. 1C) in this state, the two-component mixing container is brought into a state shown in each of FIGS. 8A, 9A to 9C, 10A to 10C, and 11A and 11B. As shown in FIG. 10B in particular, the piston member 111 and the second-component containing member 109 rotate together without the contact portions 117 getting out of the fitting grooves 196. When the piston member 111 is rotated about the axial line X, the pair of extended portions 200 provided at the second-component containing member 109 come into contact with the engaging portions 184 of the pair of engaging pieces 183 provided at the partition wall member 107 to define the rotation range of the second-component containing member 109.

Figure 10C:
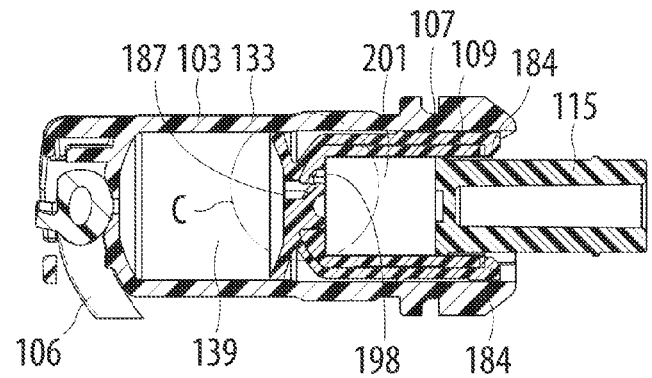
FIG. 10C is a sectional view taken along a line XC-XC in FIG. 9B.
Figure 11A:
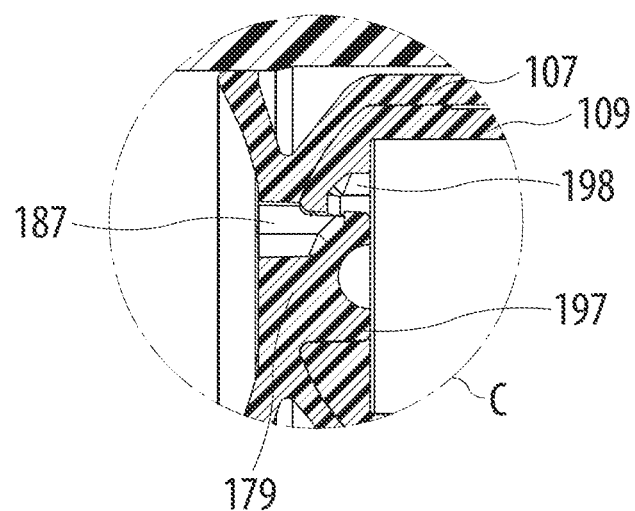
FIG. 11A is an enlarged view of a relevant portion C in FIG. 10C
Figure 11B:
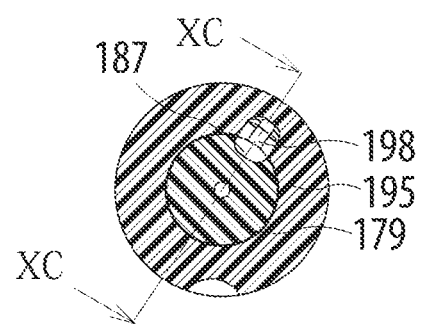
FIG. 11B is a sectional view taken along a line XIA-XIA in FIG. 10A.

As shown in FIGS. 10C and FIGS. 11A and 11B in particular, this rotation of the piston member 111 may cause the first communication passage 187 and the second communication passage 198 to communicate with each other, using a fitting surface formed between the columnar portion 179 at the central portion of the second bottom wall portion 175 of the partition wall member 107 and the circular through hole 197 in the central portion of the third bottom wall portion 195 of the second-component containing member 109. Consequently, the first communication passage 187 and the second communication passage 198 may be more reliably communicated with each other than in the conventional two-component mixing container. Further, a high processing precision is not needed for each of the partition wall member 107 and the second-component containing member 109.

As shown in FIGS. 7A and 7B, and FIG. 10B, the spring structure portions 119 and the fitting grooves 196 (FIG. 7C and FIG. 10B) are formed such that the contact portions 117 of the spring structure portions 119 get out of the fitting grooves 196 when a force of a predetermined level or higher toward the third bottom wall portion 195 is applied when the first communication passage 187 and the second communication passage 198 are in the communication state. Specifically, a taper 122 is provided at an end portion of each contact portion 117 on the side of the piston portion 113. Further, the strength of the spring force of each spring structure portion 119 is also set to allow the contact portion 117 to get out of the fitting groove 196 when the force of the predetermined level or higher toward the third bottom wall portion 195 is applied to the operating rod portion 115. Two or more of the fitting grooves 196 provided in the second-component containing member 109 have a simple, linearly extending shape. Consequently, a mold used for manufacturing the second-component containing member 109 is simple. According to this embodiment, the piston member 111 may be made to perform a rotating motion operation and a linear motion operation without the need for a complex guide groove. Assume that the second-component containing chamber 201 and the mixing chamber 139 are in a communication state. Then, when the force of the predetermined level or higher toward the third bottom wall portion 115 is applied to the operating rod portion 115 of the piston member 111, the contact portions 117 get out of the fitting grooves 196. The piston member 111 thereby moves toward the third bottom wall portion 195 of the second-component containing member 109, so that the second component may be injected into the mixing chamber 139.

FIGS. 12A to 12D show a state where the contact portions 117 of the spring structure portions 119 get out of the fitting grooves 196 and then the piston portion comes into contact with an inner wall surface of the third bottom wall portion 195 of the second-component containing member 109 when the first communication passage 187 and the second communication passage 198 are in the communication state and the force of the predetermined level or higher toward the third bottom wall portion 195 is applied to the operating rod portion 115. In this state, the partition wall member 107 is held in the fixed state with respect to the housing 103 by the holding structure (137, 181). The nozzle 105 is positioned and held at the first position by the nozzle mounting structure 106.

Figure 12A:
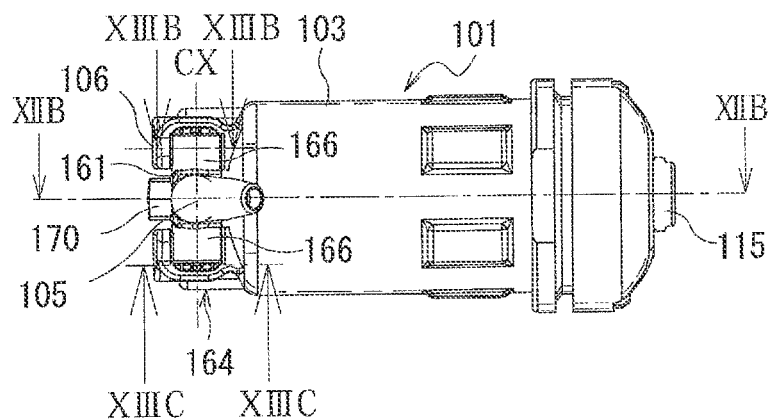
FIG. 12A is a bottom view of the two-component mixing container after the piston member has been pressed into the second-component containing member.
Figure 12B:
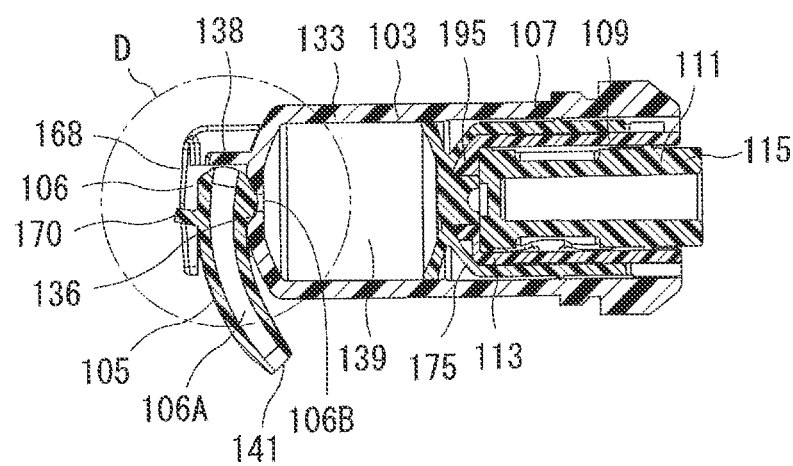
FIG. 12B is a sectional view taken along a line XIIB-XIIB in FIG. 12A.
Figure 12C:
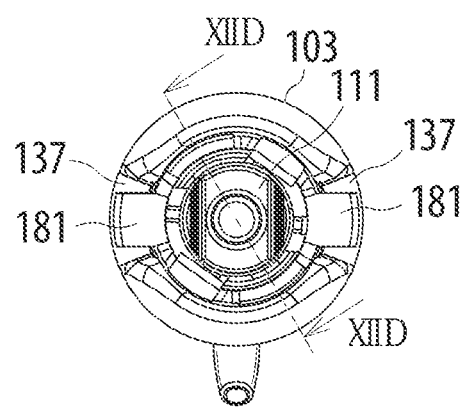
FIG. 12C is a right side view of the two-component container after the piston member has been pressed into the second-component containing member.
Figure 12D:
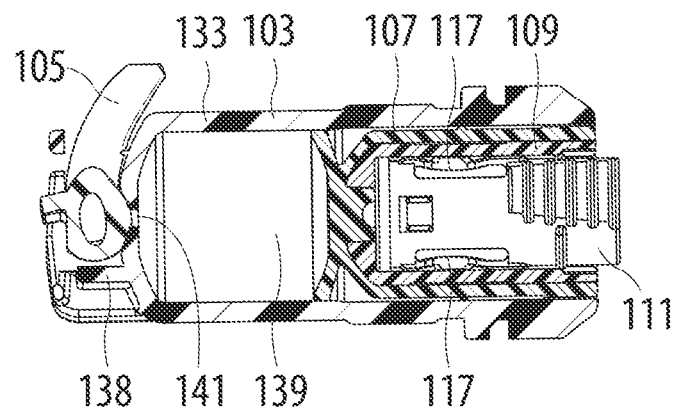
FIG. 12D is a sectional view taken along a line XIID-XIID in FIG. 12C.
Figure 13A:
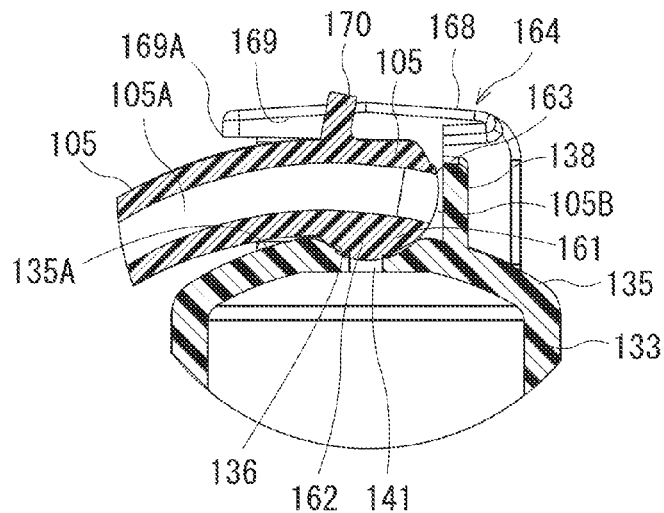
FIG. 13A is an enlarged view of a relevant portion D in FIG. 12B.
Figure 13B:
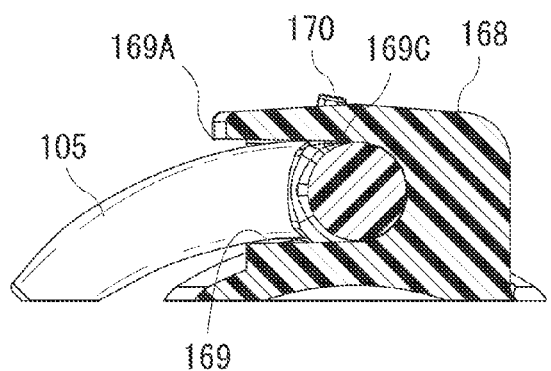
FIG. 13B is a sectional view taken along a line XIIIB-XIIIB in FIG. 12A.
Figure 13C:
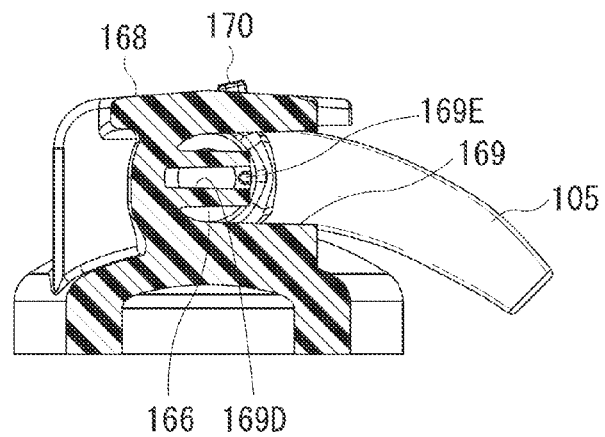
FIG. 13C is a sectional view taken along a line XIIIC-XIIIC in FIG. 12A.
Figure 14A:
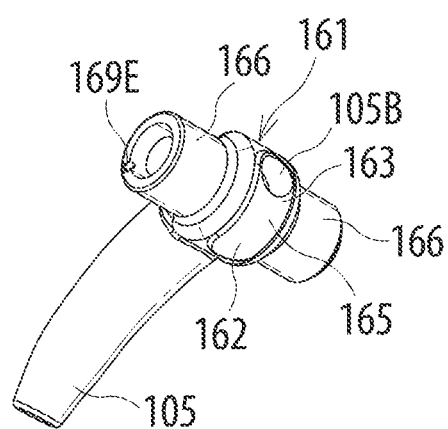
FIGS. 14A and 14B are respectively a perspective view and a right side view of portions of a nozzle and a nozzle mounting structure.
Figure 14B:
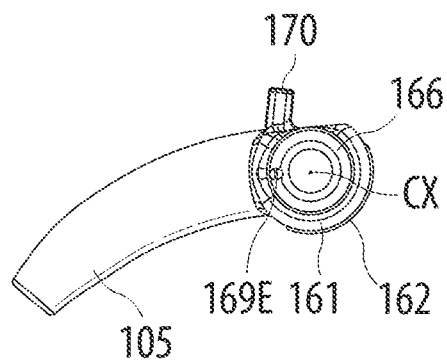
Figure 15A:
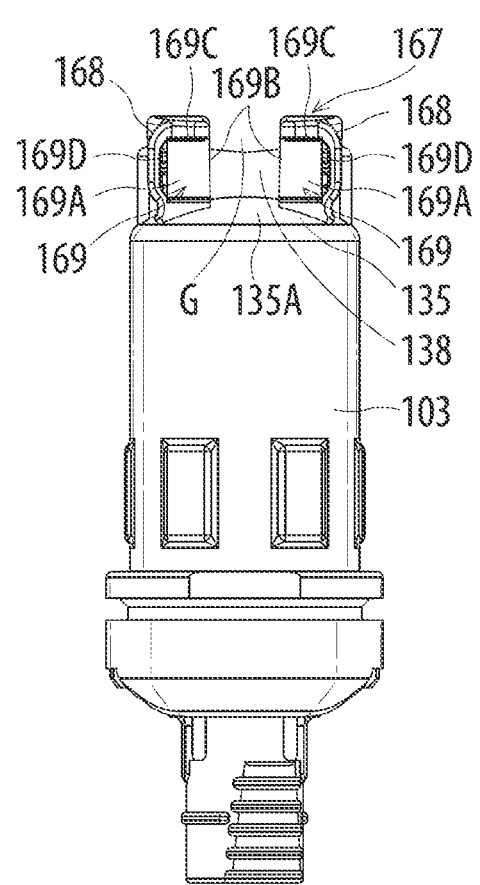
FIGS. 15A to 15C are respectively a front view and a perspective view of the two-component mixing container before the nozzle is mounted to a housing.
Figure 15B:
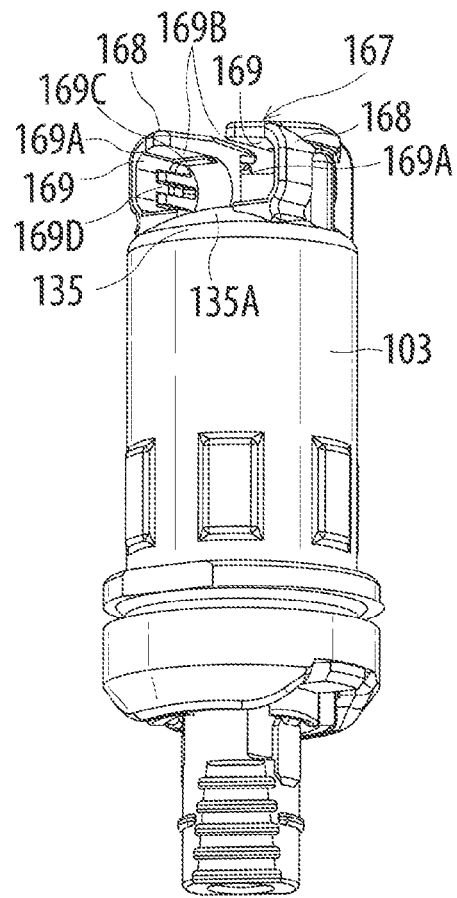
Figure 15C:
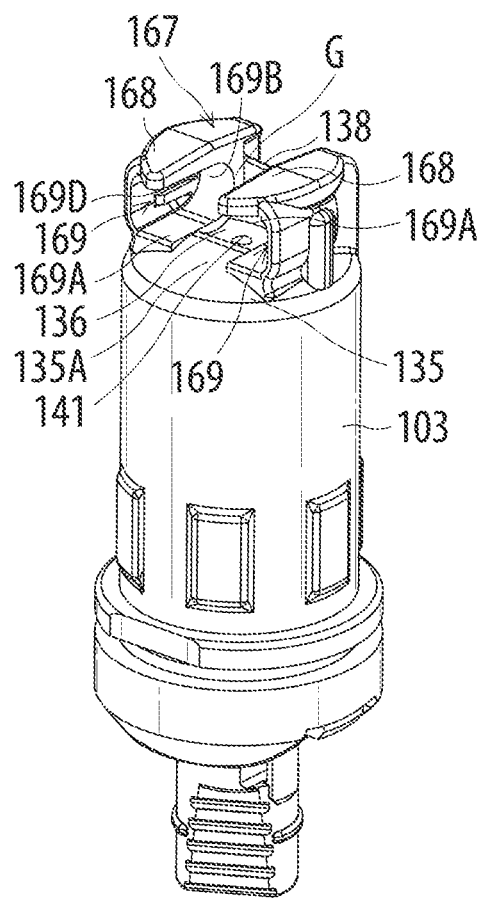

FIG. 13A shows an enlarged view of a relevant portion D in the sectional view shown in FIG. 12B, and FIGS. 13B and 13C are respectively sectional views cut at predetermined cutting positions, in order to explain the structure of the nozzle mounting structure. FIGS. 14A and 14B respectively show a perspective view and a side view of portions of the nozzle 105 and the nozzle mounting structure. FIGS. 15A to 15C are respectively a front view and perspective views of the two-component mixing container 101 before the nozzle 105 is mounted to the two-component mixing container 101. As shown in FIGS. 12A and 12B and FIG. 13A, the nozzle mounting structure 106 includes a body 161 and a body holding structure 164. As shown in FIG. 13A, the body 161 includes a closing portion 162 unitarily formed with the nozzle 105 and configured to liquid-tightly close the discharge port 141 when the nozzle 105 is disposed at the first position (position shown in FIGS. 12A to 12D), and an entrance portion 163 where an entrance 105B of a passage 105A of the nozzle 105 is formed. The body holding structure 164 has a structure configured to hold the body 161 to allow the nozzle 105 to rotate between the first position (position of the nozzle shown in FIGS. 12A to 12D) and the second position (position of the nozzle shown in FIGS. 16A to 16C)

with respect to the center of rotation. As shown in FIGS. 14A and 14B, the body 161 includes a curved convex surface 165 curved in an arc with respect to a rotation center CX. The entrance 105B of the passage 105A of the nozzle 105 opens in an end portion of the curved convex surface 165 to form the entrance portion 163. The closing portion 162 is formed by the curved convex surface 165 except the entrance portion 163. Then, as shown in FIGS. 12B, 13A, and 15C, a curved concave surface 136 is formed on an outer surface of the first bottom wall portion 135 of the housing 103 such that the curved convex surface 165 slides thereon. The discharge port 141 opens in this curved concave surface 136. The body holding structure 164 includes a pair of shaft portions 166 provided at the body 161 and extending opposite directions along a line passing through the rotation center CX, and a support portion 167 provided at the first bottom wall portion 135 of the housing 103 and configured to rotatably support the pair of shaft portions 166 and to impart on the body 161 a pressing force for pressing the curved convex surface 165 against the curved concave surface 136.

According to this embodiment, the body 161 is supported by the pair of shaft portions 166. Thus, the nozzle 105 rotates between the first position and the second position, constantly describing a same locus. Further, the curved convex surface 165 provided on the body 161 is pressed against the curved concave surface 136 provided on the first bottom wall portion 135 of the housing 103 by the pressing force imparted from the support portion 167. Thus, the mixture will not leak from between the curved convex surface 165 and the curved concave surface 136. Consequently, according to this embodiment, the nozzle 105 configured to rotate between the first position and the second position may be mounted to the housing 103 without the need for a high processing precision and a high assembly precision.

As shown in FIGS. 15A to 15C, the support portion 167 includes a pair of standing walls 168 located on both sides of the curved concave surface 136 and standing from the first bottom wall portion 135. A pair of fitting grooves 169 are formed in opposing wall portions of the pair of standing walls 168 opposing each other. The pair of fitting grooves 169 each includes a first opening portion 169A and a second opening portion 169B. The first opening portion 169A opens in one direction orthogonal to a direction where the pair of standing walls 168 extend away from the first bottom wall portion 135. The second opening portion 169B opens in a direction where the pair of standing walls 168 oppose each other. Then, inner wall surfaces of the pair of fitting grooves 169 and a section 135A of the first bottom wall portion 135 located between the pair of standing walls 168 on the side of the first opening portion 169A rather than the curved concave surface 136 are each shaped such that the pair of shaft portions 166 are tightly fitted in the pair of fitting grooves 169 when inserted into the pair of fitting grooves 169 through the first opening portions 169A of the fitting grooves 169, and the pair of shaft portions 166 are fitted in the fitting grooves 169 to allow the shaft portions 166 to rotate and to produce the pressing force when the curved convex surface 165 is fitted in the curved concave surface 136. Specifically, the section 135A of the first bottom wall portion 135 has a shape that curves to be convex toward an outside (in the direction where the pair of standing walls 168 extend from the first bottom wall portion 135). When the support portion 167 with this structure is used, the nozzle 105 may be mounted to the housing 103 just by pressing the pair of shaft portions 166 into the pair of fitting grooves 169 through the first opening portions 169A.

The body 161 and the pair of shaft portions 166 are concentrically and unitarily formed. The pair of shaft portions 166 each have a radius smaller than the radius of curvature of the curved convex surface 165. When such a configuration is adopted, the pressing force for pressing the curved convex surface 165 against the curved concave surface 136 may be reliably produced.

In this embodiment, projecting portions 169C are unitarily formed with the inner wall surfaces of the pair of fitting grooves 169, as shown in FIGS. 13B, and 15A and 15B. The projecting portions 169C are configured to come into contact with outer peripheral surfaces of the pair of shaft portions 166 to impart a force toward the first bottom wall portion 135 on the pair of shaft portions 166 when the curved convex surface 165 is fitted in the curved concave surface 136. When such projecting portions 169C are provided, the pressing force may be reliably produced. Liquid tightness between the curved concave surface 136 and the curved convex surface 165 may be thereby ensured.

As shown in FIGS. 13C and 15A and 15B, a pair of guide grooves 169D are provided in portions of the inner wall surfaces of the pair of fitting grooves 169 that oppose the second opening portions 169B. Further, as shown in FIGS. 14A and 14B, a pair of guided projections 169E to be fitted in the pair of guide grooves 169D are provided at axially outer end surfaces of the pair of shaft portions 166. In this case, when the pair of shaft portions 166 are fully fitted in the pair of fitting grooves 169 by moving the pair of guided projections 169E along the pair of guide grooves 169D, the nozzle 105 is brought to the first position. The width and the depth of each guide groove 169D and an amount of projection of each guided projection 169E are set such that the pair of guided projections 169E may get out of the pair of guide grooves 169D when the nozzle 105 is displaced into the second position. When such a pair of guide grooves 169D and such a pair of guided projections 169E are provided, the nozzle 105 may be readily assembled onto the housing 103, using a simple structure.

A projecting portion 170 is unitarily formed with the body 161. The projecting portion 170 projects in a radial direction of the body 161 and is movable in a gap G (FIGS. 15A and 15C) between the pair of standing walls 168. Then, a contact portion 138 to be contacted by the projecting portion 170 is unitarily formed with the first bottom wall portion 135 of the housing 103. The projecting portion 170 and the contact portion 138 form a stopper for preventing the nozzle 105 from being rotated in a direction opposite to the first position when the nozzle 105 is at the second position. Since such a stopper is provided, the nozzle may be reliably stopped at the second position. The stopper may be provided for at least one of the body 161 and the first bottom wall portion 135.

Figure 16A:
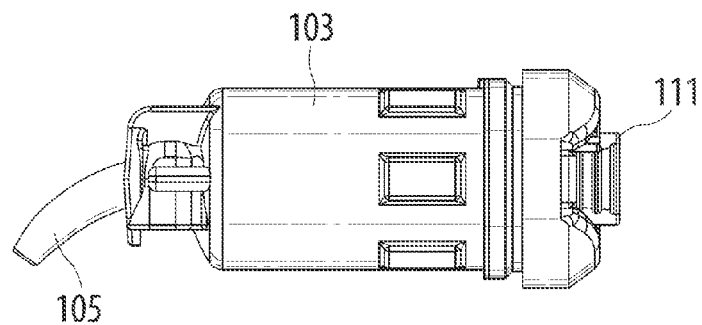
FIGS. 16A and 16B are respectively a front view and a bottom view of the two-component container when the nozzle is displaced into a second position.
Figure 16B:
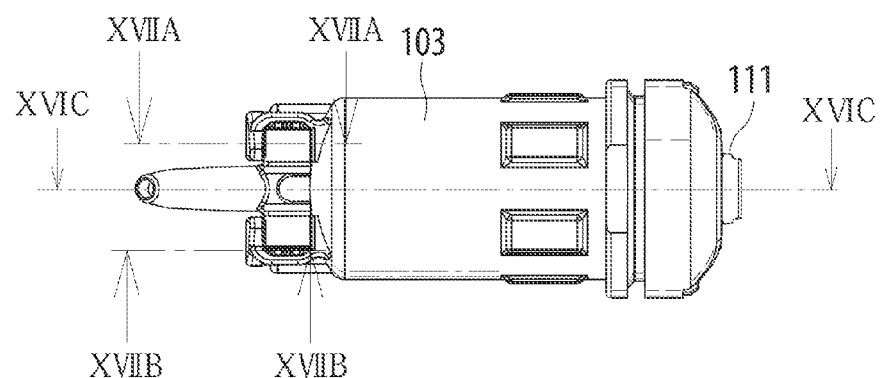
Figure 16C:
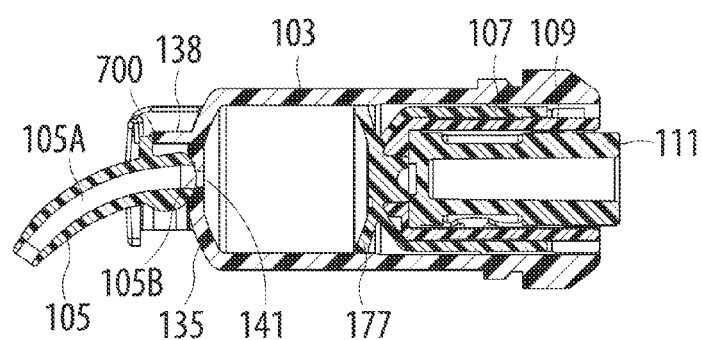
FIG. 16C is a sectional view taken along a line XVIC-XVIC in FIG. 16B.
Figure 17A:
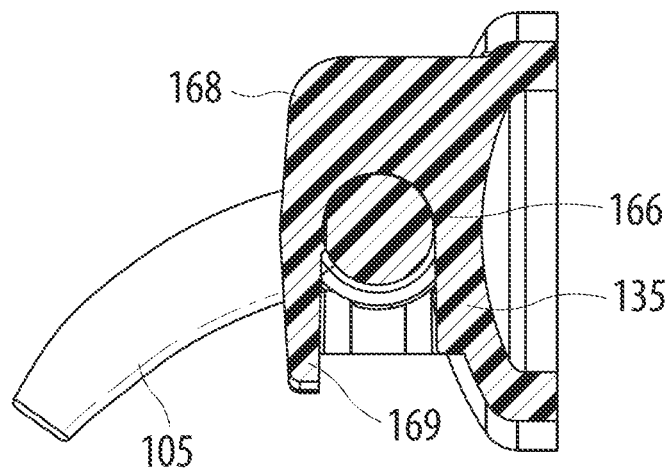
FIG. 17A is a sectional view taken along a line XVIIA-XVIIA in FIG. 16B.
Figure 17B:
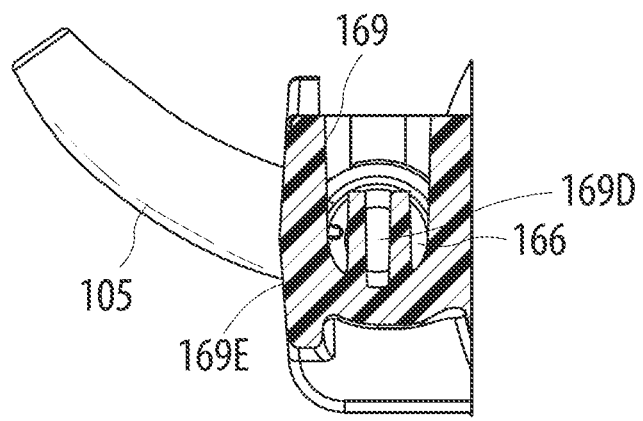
FIG. 17B is a sectional view taken along a line XVIIB-XVIIB in FIG. 16B.

When the second component (liquid material) is injected into the mixing chamber 139 as shown in FIGS. 12A to 12D, the liquid material and the powder material are mixed into the mixture (or the reaction product) by shaking well the two-component mixing container 101. When the liquid material and the powder material are sufficiently mixed, the nozzle 105 is displaced into the second position, as shown in FIGS. 16A to 16C to align the entrance 105B of the nozzle 105 and the discharge port 141, thereby forming a discharge passage. In this state, the pair of guided projections 169E have gotten out of the pair of guide grooves 169D, as shown in FIG. 175.

Figure 18A:
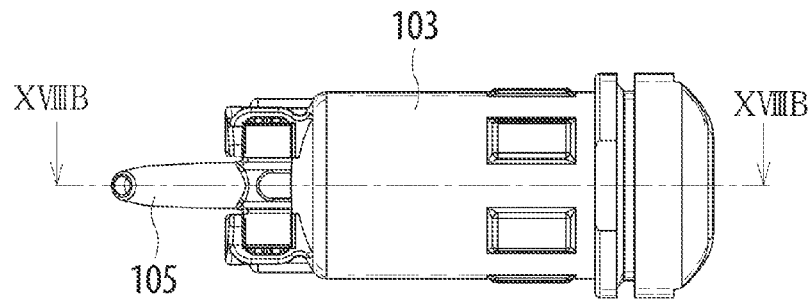
FIG. 18A is a bottom view of the two-component mixing container when the piston member is pushed by a dedicated extruder to move a partition wall portion of the partition wall member to a first bottom wall portion of the housing.
Figure 18B:
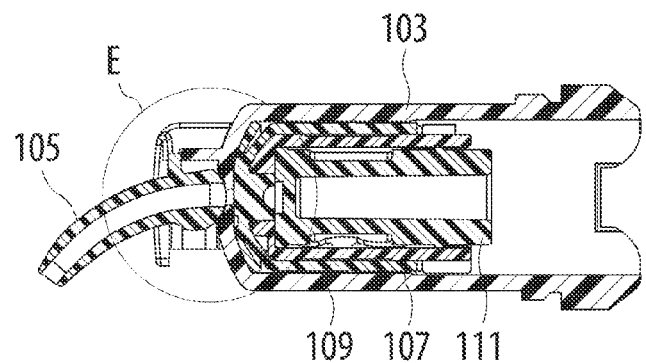
FIG. 18B is a sectional view taken along a line XVIIIB-XVIIIB in FIG. 18A.
Figure 18C:
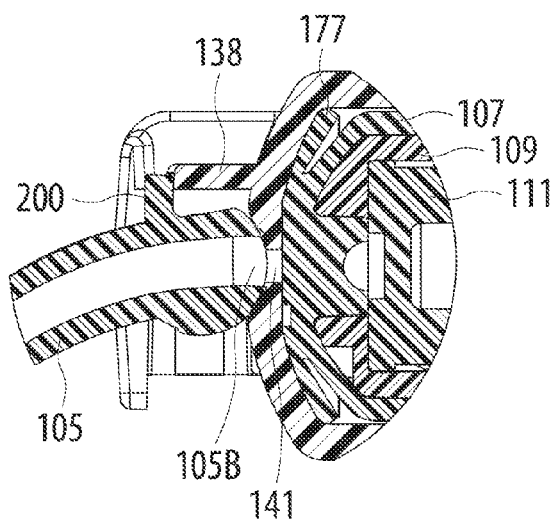
FIG. 18C is an enlarged view of a relevant portion E in FIG. 18B.
Figure 19:
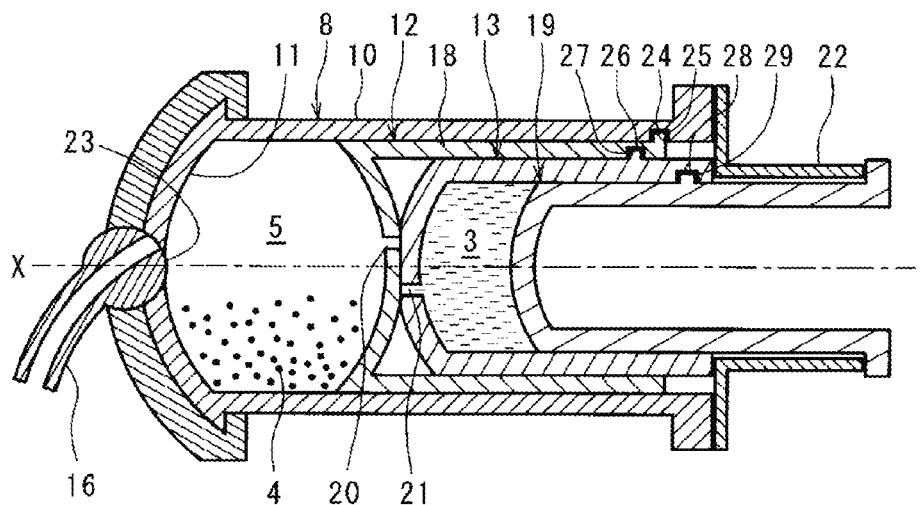
FIG. 19 is FIG. 10 in Japanese Patent No. 4956616.
Figure 20A:
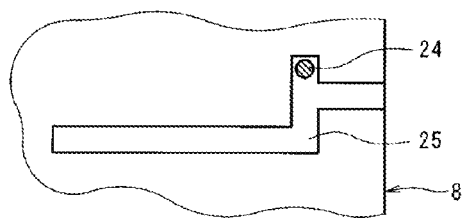
FIGS. 20A to 20C are respectively FIGS. 11A to 11C in Japanese Patent No. 4956616.
Figure 20B:
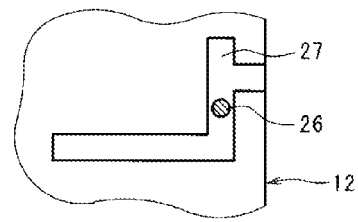
Figure 20C:
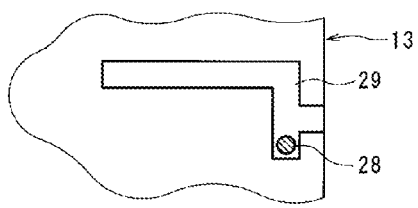

The two-component mixing container 101 shown in FIGS. 16A to 16C is mounted to a dedicated extruder not shown. The dedicated extruder includes a piston configured to push the piston member 111. FIGS. 18A to 18C show diagrams used for explaining a state where the piston member 111 has been pushed to move the partition wall portion 177 of the partition wall member 107 to the first bottom wall portion 135 of the housing 103. The partition wall portion 177 of the partition wall member 107 in this embodiment is shaped to deform according to the shape of an inner wall surface of the first bottom wall portion 135 of the housing 103 when the piston member 111 is moved toward the first bottom wall portion 135 to discharge the mixture to the outside from the mixing chamber 139 through the nozzle 105 (refer to FIGS. 18B and 18C). Consequently, a maximum amount of the mixture may be discharged from the mixing chamber 139.

When the piston member 111 is moved toward the first bottom wall portion 135, the pair of projecting pieces 181 are bent by pressing the piston member 111 toward the first bottom wall portion 135 by the force of the predetermined level or higher. In this embodiment, the pair of projecting pieces 181 are provided in the vicinity of the second opening portion 171 of the second cylindrical portion 173 of the partition wall member 107 and extend radially outward. The bent pair of projecting pieces 181 thereby enter into the housing 103. Since such a structure of bending the pair of projecting pieces 181 is adopted, a structure for releasing fixation is simplified.

Figure 5A:
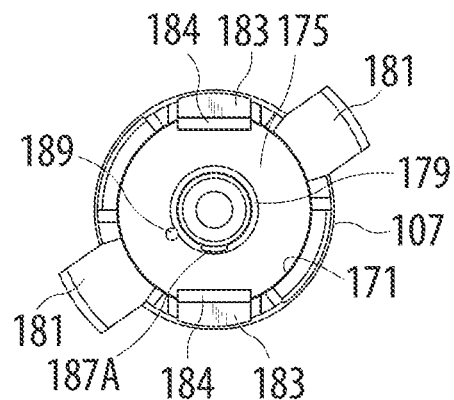
FIGS. 5A to 5C are respectively a plan view, a perspective view, and a bottom view of a partition wall member.
Figure 5B:
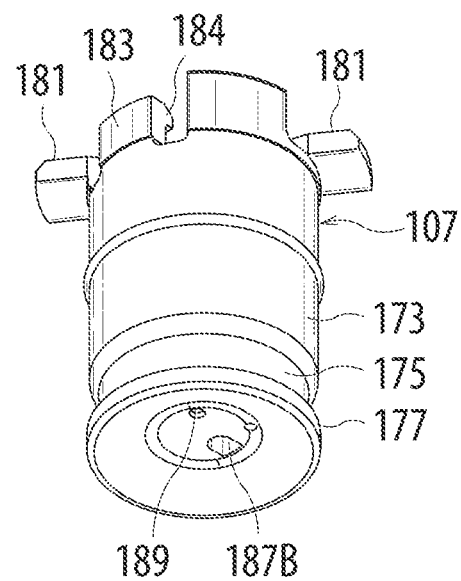
Figure 5C:
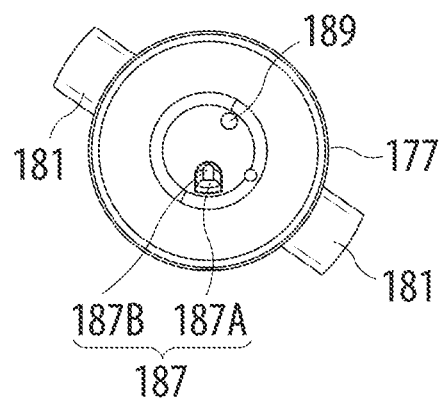

In this embodiment, a through hole 189 for air extraction is formed in the second bottom wall portion 175 of the partition wall member 107, as shown in FIGS. 5A to 5C. The through hole 189 is configured to communicate the mixing chamber 139 and a gap between the second bottom wall portion 175 and the third bottom wall portion 195 of the second-component containing member 109. With this arrangement, the air extraction is performed using the gap. Thus, when injecting the second component into the mixing chamber 139, air extraction may be readily performed without preparing for a special structure.

According to the present invention, the first communication passage and the second communication passage may be communicated with each other, using the fitting surface formed between the columnar portion provided at the central portion of the second bottom wall portion of the partition wall member and the circular through hole provided in the central portion of the third bottom wall portion of the second-component containing member. Consequently, the first communication passage and the second communication passage may be more reliably communicated with each other than in the conventional two-component mixing container. No high processing precision is needed for each of the partition wall member and the second-component containing member.

While the preferred embodiment of the invention has been described with a certain degree of particularity with reference to the drawings, obvious modifications and variations are possible in light of the above teachings. It is therefore to be understood that within the scope of the appended claims, the invention may be practiced otherwise than as specifically described.

What is claimed is:

1. A two-component mixing container comprising:
a housing including:
a first cylindrical portion having a first opening portion at one end thereof;
a mixing chamber provided inside the housing, and configured to contain a first component and to mix the first component and a second component when the second component is injected into the one end of the first cylindrical portion; and
a first bottom wall portion closing the other end of the first cylindrical portion and having a discharge port configured to discharge the mixture of the first component and the second component from the mixing chamber;
a nozzle provided at the housing and configured to discharge the mixture, whereby the mixture comes out of the discharge port and is discharged through the nozzle;
a partition wall member configured to liquid-tightly slide inside the mixing chamber and including:
a second cylindrical portion having a second opening portion at one end thereof; and
a second bottom wall portion closing the other end of the second cylindrical portion;
a second-component containing member fitted in the second cylindrical portion and including:
a third cylindrical portion having a third opening portion at one end thereof;
a third bottom wall portion closing the other end of the third cylindrical portion; and
a second-component containing chamber provided inside the second-component containing member and configured to contain the second component;
a piston member including:
a piston portion located at one end of the piston member and configured to be inserted into the third cylindrical portion from the third opening portion and liquid-tightly slide inside the third cylindrical portion; and
an operating rod portion located at the other end of the piston member and projecting out from the third opening portion; and
a holding structure configured to hold the partition wall member in a fixed state with respect to the housing until the second component is injected into the mixing chamber and to release the fixed state to allow the mixture to be discharged through the nozzle, wherein:
the second bottom wall portion of the partition wall member is formed with a first communication passage and the third bottom wall portion of the second-component containing member is formed with a second communication passage, the first communication passage and the second communication passage communicating with each other when the two-component containing member and the partition wall member come into a predetermined positional relationship, thereby allowing the second component to flow into the mixing chamber;
a columnar portion extending along the second cylindrical portion is unitarily formed with a central portion of the second bottom wall portion;
a circular through hole is formed in a central portion of the third bottom wall portion, whereby the columnar portion is fitted into the circular through hole;
the first communication passage is formed in the second bottom wall portion and the columnar portion such that one end of the first communication passage opens in an outer surface of the columnar portion and the other end of the first communication passage opens in an outer wall surface of the second bottom wall portion;
the second communication passage is formed in an inner wall of the third bottom wall portion such that one end of the second communication passage communicates with the circular through hole and the other end of the second communication passage opens toward the second-component containing chamber; and
the columnar portion and the circular through hole are shaped and sized such that the third cylindrical portion rotates with respect to the columnar portion in a liquid-tight state until the one end of the first communication passage and the one end of the second communication passage communicate with each other.

2. The two-component mixing container according to claim 1, wherein
a through hole for air extraction is formed in the second bottom wall portion, and is configured to communicate the mixing chamber and a gap between the second bottom wall portion and the third bottom wall portion.

* * * * *